(12) United States Patent
Nuñez et al.

(10) Patent No.: US 7,244,557 B2
(45) Date of Patent: Jul. 17, 2007

(54) METHOD OF SCREENING MODULATORS OF NOD1 SIGNALING

(75) Inventors: Gabriel Nuñez, Ann Arbor, MI (US); Naohiro Inohara, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 73 days.

(21) Appl. No.: 10/845,799

(22) Filed: May 14, 2004

(65) Prior Publication Data

US 2005/0009065 A1   Jan. 13, 2005

Related U.S. Application Data

(60) Provisional application No. 60/470,334, filed on May 14, 2003.

(51) Int. Cl.
 *C12Q 1/00* (2006.01)
(52) U.S. Cl. .......................................................... 435/4
(58) Field of Classification Search ...................... None
 See application file for complete search history.

(56) References Cited

U.S. PATENT DOCUMENTS

2004/0235735 A1* 11/2004 Girardin et al.

OTHER PUBLICATIONS

Takeda and Akira, Genes Cells 6:733 [2001].
Girardin et al., Trends Microbiol. 10:193 [2002].
Inohara and Nunez, Nat. Rev. Immunol. 3:371 2003 .
Staskawicz et al., Science 292:2285 [2001].
Bertin et al., J. Biol. Chem. 274:12955 [1999].
Inohara et al., J. Biol. Chem. 274:14560 [1999].
Kobayashi et al., Nature 416:194 [2002].
Inohara et al., J. Biol. Chem. 278:5509 [2003].
Girardin et al., J. Biol. Chem. 278:8869 [2003].
Girardin et al., EMBO Rep. 2:736 [2001].
Schleifer and Kandler, Bacteriological Reviews 36:407 [1972].
Kitaura et al., J. Med. Chem. 25:335 [1982].
Shanahan, Science 289:1311 [2000].
Laitinen et al., Nat Genet May 2001;28(1):87-91.
Leaves et al., Eur J Hum Genet. Mar. 2002; 10(3):177-82.
Inohara et al., J. Biol. Chem. 276:2551 [2001].
Raetz et al., Ann. Rev. Biochem. 71:635 [2002].
Valvano et al., Microbiology 148:1979 [2002].
Mine et al., J Antibiot (Tokyo) Aug. 1983;36(8):1045-50.
Mine et al., J Antibiot (Tokyo) Aug. 1983;36(8):1059-66.
Inamura et al., Cancer Immunol Immunother 1989;28(3):164-70.
Blaney and Turk, Immunopharmacol Immunotoxicol Aug. 1995;17(3):451-69.
Kumar et al., Neoplasma 1997;44(5):319-23.
Maeda et al., Biol Pharm Bull Feb. 1994;17(2):173-9.
Inamura et al., J Biol Response Mod Aug. 1985;4(4):408-17.
Talmadge et al., Cancer Immunol Immunother 1989;28(2):93-100.
Schultz et al., J Immunopharmacol 1986;8(4):515-28.
Schroeder et al., New Engl. J. Med., 317, 1625 (1987).
Sutherland et al., Med. Clin. North Amer., 74, 119 (1990).
Hirschfeld et al., J. Immunol. 165:618 [2000].
Heilman et al., Mol. Microbiol. 24:1013 [1997].
Atrih et al., J. Bact. 181:3956 [1999].

* cited by examiner

*Primary Examiner*—Robert S. Landsman
*Assistant Examiner*—Bruce Hissong
(74) *Attorney, Agent, or Firm*—Medlen & Carroll, LLP

(57) ABSTRACT

The present invention relates to intracellular signaling molecules, in particular the Nod1 protein. The present invention provides methods of identifying modulators of Nod1 signaling. The present invention further provides methods of altering Nod1 signaling.

6 Claims, 6 Drawing Sheets

METHOD OF SCREENING MODULATORS OF NOD1 SIGNALING

This Application claims priority to provisional patent application Ser. No. 60/470,334, filed May 14, 2003, which is herein incorporated by reference in its entirety.

This patent application was supported in part by grants DK-61707 and GM-60421 from the National Institutes of Health. The government has certain rights in the invention.

FIELD OF THE INVENTION

The present invention relates to intracellular signaling molecules, in particular the Nod1 protein. The present invention provides methods of identifying modulators of Nod1 signaling. The present invention further provides methods of altering Nod1 signaling.

BACKGROUND OF THE INVENTION

There are more than 80 different known autoimmune and inflammatory diseases that are characterized by abnormal triggering of an inflammatory response that attacks the host's own organs or tissues.

Examples of autoimmune and inflammatory diseases include rheumatoid arthritis, inflammation of the heart (myocarditis), asthma, inflammatory bowel disease such as Crohn's disease and ulcerative colitis, systemic lupus erythematosus, rheumatic fever, autoimmune hemolytic anemia, idiopathic thrombocytopenic purpura, and postviral encephalomyelitis.

There are a number of treatment options for inflammatory diseases including medications, rest and exercise, and surgery. The type of treatment depends on several factors, including the type of disease, the person's age, type of medications he or she is taking, overall health, medical history and severity of symptoms. Common medications include nonsteroidal anti-inflammatory drugs (NSAIDs such as aspirin, ibuprofen or naproxen), corticosteroids (such as prednisone), salicylates, antimalarial medications (such as hydroxychloroquine), and other medications including gold, methotrexate, sulfasalazine, penicillamine, cyclophosphamide, infliximab, etanercept and cyclosporine. However, many of the existing treatments have unpleasant side effects and are not effective.

Clearly there is a great need for identification of the molecular basis of inflammatory disease. There is also a need for new, more effective treatments with fewer side effects than the existing treatments.

SUMMARY OF THE INVENTION

The present invention relates to intracellular signaling molecules, in particular the Nod1 protein. The present invention provides methods of identifying modulators of Nod1 signaling. The present invention further provides methods of altering Nod1 signaling.

Accordingly, in some embodiments the present invention provides a method of screening compounds, comprising providing a cell expressing Nod1; and a plurality of test compounds; and contacting the cell with the plurality of test compounds; and determining the level of Nod1 activity in the cell in response to the test compound. In some embodiments, the Nod1 activity comprises activation of NF-κB. In some embodiments, the activation of NF-κB is detected using a reporter gene assay. The present invention is not limited to a particular test compound. Indeed, a variety of test compounds are contemplated including, but not limited to, a peptide comprising a glutamine-diaminopimelic acid dipeptide and a peptide comprising a glutamic acid-diaminopimelic acid dipeptides (e.g., iE-DAP, iQ-DAP, an analog of iE-DAP or iQ-DAP, or a small molecule mimetic of iE-DAP or iQ-DAP). In certain embodiments, the Nod1 activity is increased in response to the test compound, while in other embodiments, the Nod1 activity is decreased in response to the test compound.

The present invention further provides a method of modulating Nod1 signaling in a subject, comprising providing a compound that is capable of altering a subject's Nod1 activity; and administering the compound to a subject under conditions such that the subject's Nod1 activity is altered. In some embodiments, the subject's Nod1 activity is increased in response to the compound. In certain embodiments, the subject exhibits symptoms of an inflammatory disease (e.g., Crohn's disease or asthma). In some preferred embodiments, the administering the compound to the subject results in a decrease in the subject's symptoms of an inflammatory disease. In some embodiments, the subject has a variant Nod2 allele. The present invention is not limited to a particular compound. Indeed, a variety of compounds are contemplated including, but not limited to, a peptide comprising a glutamine-diaminopimelic acid dipeptide and a peptide comprising a glutamic acid-diaminopimelic acid dipeptides (e.g., iE-DAP, iQ-DAP, an analog of iE-DAP or iQ-DAP, or a small molecule mimetic of iE-DAP or iQ-DAP).

GENERAL DESCRIPTION OF THE INVENTION

Figure 1:
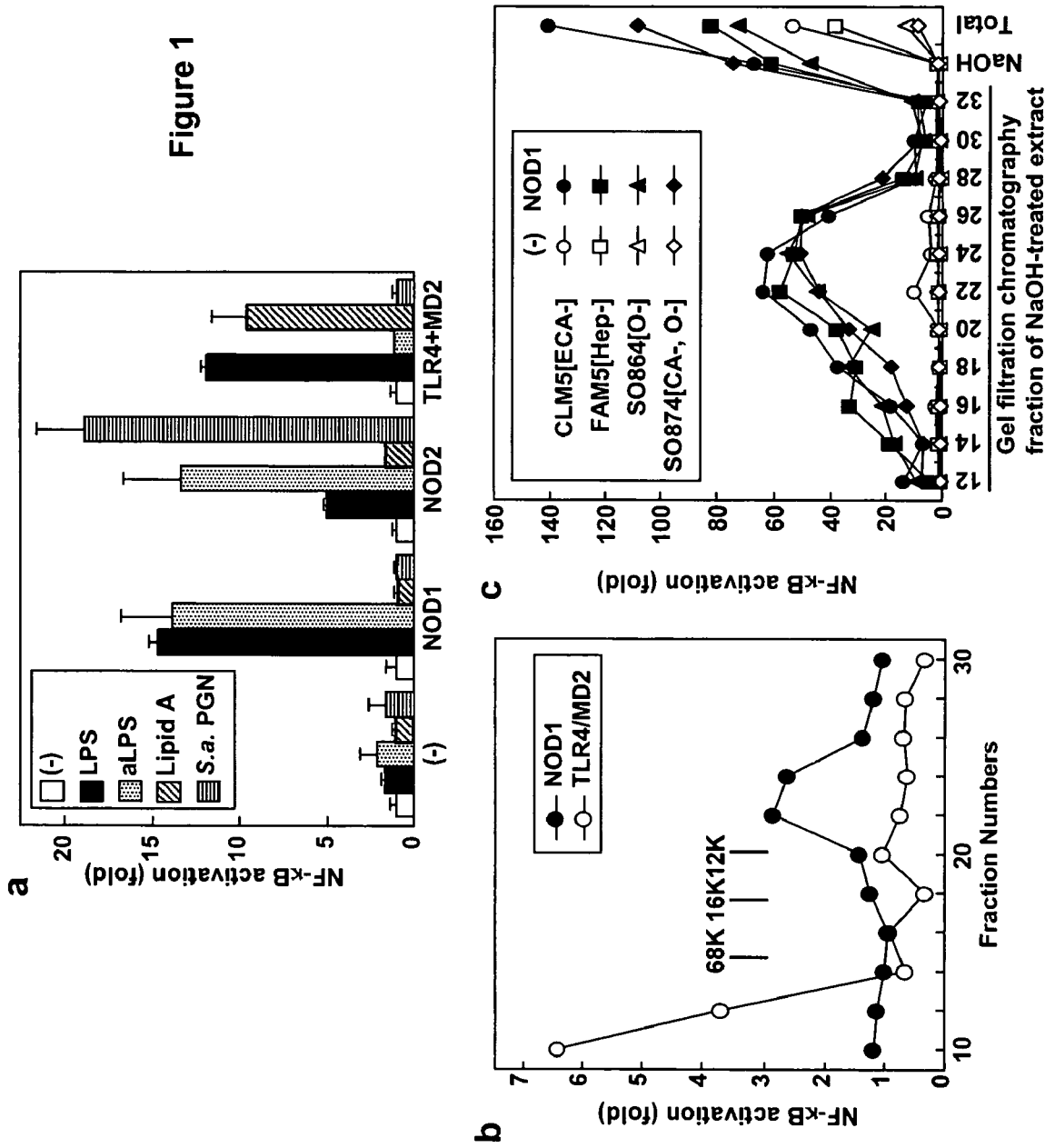
FIG. 1 shows recognition of bacterial components by NOD1, NOD2 and TLR4. A) NOD1 and TLR4 recognize different bacterial components. B) The graph shown represents the ability of each fraction of E. coli O55:B5 LPS separated by SUPEROSIE 12 gel-filtration to induce NOD1 or TLR4/MD-2-dependent NF-κB activation. The NF-κB-dependent transcriptional activity of vector-transfected cells in the absence of the ligand is given as 1. C) The graphic represents the ability from each fraction to induce NOD1-dependent NF-κB activation. The transcriptional activity in the absence of the ligand is given as 1.

The innate immune system represents a first-time host defense that recognizes invading pathogens and triggers a defense response in the host aimed at clearing the infection. Animals and plants possess specialized host receptors recognizing conserved molecules that are expressed exclusively by microorganisms or parasites (Takeda and Akira, Genes Cells 6:733 [2001]; Girardin et al., Trends Microbiol. 10:193 [2002]). Those molecules, known as microbial pathogen-associated molecular patterns (PAMPs), help to establish the distinction between pathogens and host cells. Among vertebrates and invertebrates, detection of microbes is mediated by specific host pattern-recognition receptors (PRRs) in intra-cellular compartments or at the cell surface (Girardin et al., supra). Toll-like receptors (TLRs) expressed on the surface of innate immune cells play an important role in the recognition of PAMPs and activation of innate immunity (Takeda and Akira, supra; Girardin et al., surpa). Little is known about how the host cell can sense and respond to internalized bacteria. NODs, including NOD1 and NOD2, are members of an emerging family of proteins that have been implicated in intracellular recognition of bacterial components (Inohara and Nunez, Nat. Rev. Immunol. 3:371 [2003]) NODs exhibit structural homology to a class of proteins (R proteins) that are encoded by plant disease-resistance genes (Inohara and Nunez, Nat. Rev. Immunol. 3:371 [2003]). Plant R proteins recognize distinct effectors molecules from invading pathogens and mediate a defense response resulting in plant disease resistance (Staskawicz et al., Science 292:2285 [2001]). NOD1, also called CARD4, is composed of an NH$_2$-terminal caspase-recruitment domain (CARD), a centrally located nucleotide-binding oligomerization domain (NOD) and multiple COOH-terminal leucine-rich repeats (LRRs). NOD1 is ubiquitously expressed in multiple tissues (Bertin et al., J. Biol. Chem. 274:12955 [1999]; Inohara et al., J. Biol. Chem. 274:14560 [1999]). Transient expression of NOD1 in mammalian cells induces NF-κB activation, an activity that is mediated through homophilic CARD-CARD interactions with RICK/RIP2/CARDIAK, a CARD-containing protein kinase interacting with the IKK complex (Bertin et al., supra; Inohara et al., J. Biol. Chem. 274:14560 [1999]). A role for RICK in NOD1 signaling is supported by analysis of cells derived from mutant mice deficient in RICK (Kobayashi et al., Nature 416:194 [2002]). The muramyldipeptide MurNAc-L-Ala-γ-D-Gln (MDP), a moiety conserved in the cell wall peptidoglycan (PGN) of practically all bacteria, has been identified as the essential bacterial structure recognized by NOD2 (Inohara et al., J. Biol. Chem. 278:5509 [2003]; Girardin et al., J. Biol. Chem. 278:8869 [2003]). NOD1 has been suggested to mediate responsiveness to lipopolysaccharides (LPS) from several Gram-negative bacteria through its COOH-terminal LRRs (Inohara et al., J. Biol. Chem. 276:2251 [2001]; Girardin et al., EMBO Rep. 2:736 [2001]).

Experiments conducted during the course of development of the present invention identified PGN containing γ-D-glutamy-meso-diaminopimelic acid (iE-DAP), as being recognized by a NOD1-mediated pathway. The dipeptide IE-DAP is uniquely present in PGN from certain bacteria including Gram-negative *bacilli*. These results indicate that NOD1 acts as an intracellular PRR for a subset of bacteria through the detection of iE-DAP. MDP, the moiety recognized by NOD2, is almost universally present in PGNs from both Gram-positive and Gram-negative bacteria, iE-DAP is known to exist only in particular bacteria including common Gram-negative bacteria, such as *E. coli*, and several Gram-positive bacteria such as *B. subtilis* or *L. monocytogenes*. The present invention is not limited to a particular mechanism. Indeed, an understanding of the mechanism is not necessary to practice the present invention. Nonetheless, it is contemplated that NOD1 mediates the host response to a subset of microbes whereas NOD2 can elicit broad recognition of bacteria. These results indicate that both NOD1 and NOD2 act as cytosolic PRRs that recognize highly conserved PGN structures present in all or large populations of bacteria.

PGNs from most Gram-negative bacteria and certain Gram-positive bacteria such as *B. subtilis* contain a DAP residue whereas a Lys is present at the same position in most Gram-positive bacteria (Schleifer and Kandler, Bacteriological Reviews 36:407 [1972]). The present invention is not limited to a particular mechanism. Indeed, an understanding of the mechanism is not necessary to practice the present invention. Nonetheless, it is contemplated that the difference in the charges between DAP and Lys may explain the specific recognition of DAP-containing PGN by NOD1. Recent studies have shown that the *Drosophila* immune system detects Gram-negative and Gram-positive bacteria through specific recognition of PGN. This is reminiscent to the recognition of bacteria mediated through NOD1 in mammals. Specific recognition of DAP-type and Lys-type in flies relies on peptidoglycan recognition proteins (PGRPs) acting upstream of the Toll and immuno-deficiency (Imd) signaling pathways. This indicates that selective host recognition of bacteria based on PGN structures is evolutionarily conserved.

NOD1 and NOD2 are structurally related to cytosolic plant R proteins. These plant proteins recognize distinct effector molecules from pathogenic bacteria and elicit a defense response against the invading pathogen (Staskawicz et al., Science 292:2285 [2001]). In contrast, human NOD1 and NOD2 recognize conserved structures shared by many pathogens. The present invention is not limited to a particular mechanism. Indeed, an understanding of the mechanism is not necessary to practice the present invention. Nonetheless, it is contemplated that this dichotomy between animals and plants could explain why plant genomes contain greater than 150 NOD-LRR proteins, whereas the human genome possesses only approximately 25 genes encoding NOD-LRR proteins (Inohara and Nunez, Nat. Rev. Immunol. 3:371 [2003]).

Both DMP and MDP are known to induce the resistance against various pathogens and function as immuno-adjuvants to enhance immunoglobulin production (Adam, A. "Modern Concepts in Immunology Vol. I Synthetic Adjuvants" John Wiley & Sons, Inc. 1-58 [1985]). Lipophilic forms of DMP containing the core dipeptide iE-DAP recognized by NOD1 are known to induce the secretion of cytokines including interleukin-6 and TNF-α in immune cells (Kitaura et al., J. Med. Chem. 25:335 [1982]; Adam, supra). The present invention is not limited to a particular mechanism. Indeed, an understanding of the mechanism is not necessary to practice the present invention. Nonetheless, it is contemplated that this suggests that NOD1, which is expressed in spleen cells, bone marrow-derived macrophages and a variety of epithelial cells plays a role in coupling innate and adaptive immune responses in a similar manner to that reported for TLRs. Accordingly, in some embodiments, PGN-derived peptides are delivered to the cytosol for NOD1 recognition from extracellular sites or phagocytosed bacteria. Because the LRRs are required for recognition of iE-DAP, PGN-derived fragments may interact directly with NOD1 through its LRRs, or indirectly via cellular factors. Chronic inflammation of the intestinal tract observed in Crohn's disease, which is associated with NOD2 mutations, can be reduced by oral administration of certain bacteria, such as *Lactococcus lactis*, which contain DAP-type PGN (Shanahan, Science 289:1311 [2000]).

In some embodiments, because both NOD1 and NOD2 signal through RICK to activate identical or similar responses (Kobayashi et al., supra), the beneficial effect induced by probiotic bacteria is elicited in through complementation of deficient NOD2 function via NOD1 signaling. The present invention is not limited to a particular mechanism. Indeed, an understanding of the mechanism is not necessary to practice the present invention. Nonetheless, it is contemplated that, given that the PGN-derived structures recognized by NOD1 and NOD2 are distinct and non-overlapping, deficient NOD2 function observed in patients with Crohn's disease can be restored through stimulation of NOD1 signaling at intestinal sites with iE-DAP or iE-DAP analogs. In other embodiments, ligands, inhibitors and activators of Nod1 find use in the treatment of inflammatory diseases in addition to Crohn's disease. For example, a region near the location of Nod1 gene at human chromosomal 7 have been shown to be linked to susceptibility to asthma (See e.g., Laitinen et al., Nat Genet 2001 May;28 (1):87–91; Leaves et al., Eur J Hum Genet. 2002 March;10 (3):177–82). Accordingly, in some embodiments, enhancers of Nod1 activity are used to treat asthma. In addition, FK565, a peptide ligand similar to those shown in experiments conducted during the course of development of the present invention to activate Nod1, has been shown to be involved in a variety of immune responses including resistance against pathogens (See e.g., Mine et al., J Antibiot (Tokyo) 1983 August;36(8):1045–50 and Mine et al., J Antibiot (Tokyo) 1983 August;36(8):1059–66), secretion of several cytokines (Inamura et al., Cancer Immunol Immunother 1989;28(3):164–70; Blaney and Turk, Immunopharmacol Immunotoxicol 1995 August;17(3):451–69; Kumar et al., Neoplasma 1997;44(5):319–23; Maeda et al., Biol Pharm Bull 1994 February; 17(2):173–9), tumoricidal properties of macrophages and other immune modulators (Inamura et al., J Biol Response Mod 1985 August;4(4):408–17; Talmadge et al., Cancer Immunol Immunother 1989;28(2): 93–100; Schultz et al., J Immunopharmacol 1986;8(4): 515–28). Accordingly, it is contemplated that modulators of Nod1 activity find use in the treatment of a variety of inflammatory diseases and processes.

Definitions

To facilitate understanding of the invention, a number of terms are defined below.

As used herein, the term "activates NF-κB," when used in reference to any molecule that activates NF-κB, refers to a molecule (e.g., a protein) that induces the activity of the NF-κB transcription factor through a cell signaling pathway. Assays for determining if a molecule activates NF-κB utilize, for example, NF-κB responsive reporter gene constructs. Suitable assays include, but are not limited to, those described in the Experimental section below.

As used herein, the term "activity of Nod1" refers to any activity of wild type Nod1. The term is intended to encompass all activities of Nod1 (e.g., including, but not limited to, activating NF-kB).

The term "apoptosis" means non-necrotic cell death that takes place in metazoan animal cells following activation of an intrinsic cell suicide program. Apoptosis is a normal process in the development and homeostasis of metazoan animals. Apoptosis involves characteristic morphological and biochemical changes, including cell shrinkage, zeiosis, or blebbing, of the plasma membrane, and nuclear collapse and fragmentation of the nuclear chromatin, at intranucleosomal sites, due to activation of an endogenous nuclease.

As used herein, the term "symptoms of Crohn's disease" refers to symptoms associated with Crohn's disease, including, but not limited to abdominal pain, diarrhea, rectal bleeding, weight loss, fever, loss of appetite, and other more serious complications, such as dehydration, anemia and malnutrition. A number of such symptoms are subject to quantitative analysis (e.g., weight loss, fever, anemia, etc.). Some symptoms are readily determined from a blood test (e.g., anemia) or a test that detects the presence of blood (e.g., rectal bleeding).

The phrase "under conditions such that symptoms of Crohn's disease are reduced" refers to a qualitative or quantitative reduction in detectable symptoms (e.g., "symptoms of Crohn's disease"), including but not limited to a detectable impact on the rate of recovery from disease (e.g., rate of weight gain).

As used herein, the term "mimetic" refers to a small molecule compound that mimics the binding or interaction of a ligand with its target. For example, a mimetic of a peptide inhibitor of a dipeptide of the present invention (e.g., iE-DAP or iQ-DAP) is a small molecule that binds to the same site on Nod1 as does the peptide or is recognized by Nod1 in the same way as the peptide (e.g., causes a similar signaling event). In some preferred embodiments, mimetic compounds are those in which the peptide cycle is replaced by any non-peptide scaffold that allows comparable positioning of functional equivalents (e.g., charge groups) of the amino acids of the Nod1 ligands of the present invention.

The term "gene" refers to a nucleic acid (e.g., DNA) sequence that comprises coding sequences necessary for the production of a polypeptide or precursor (e.g., Nod1). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (mRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

As used herein, the term "peptide" refers to a polymer of two or more amino acids joined via peptide bonds or modified peptide bonds. As used herein, the term "dipeptides" refers to a polymer of two amino acids joined via a peptide or modified peptide bond.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified", "mutant", and "variant" refer to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions with its various ligands and/or substrates.

The term "polymorphic locus" is a locus present in a population that shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding Nod1 includes, by way of example, such nucleic acid in cells ordinarily expressing Nod1 where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets that specify stop codons (i.e., TAA, TAG, TGA).

As used herein, the term "purified" or "to purify" refers to the removal of contaminants from a sample. For example, Nod1 antibodies are purified by removal of contaminating non-immunoglobulin proteins; they are also purified by the removal of immunoglobulin that does not bind Nod1. The removal of non-immunoglobulin proteins and/or the removal of immunoglobulins that do not bind Nod1 results in an increase in the percent of Nod1-reactive immunoglobulins in the sample. In another example, recombinant Nod1 polypeptides are expressed in bacterial host cells and the polypeptides are purified by the removal of host cell proteins; the percent of recombinant Nod1 polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four consecutive amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, NY, pp 9.31–9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39–7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign gene that is placed into an organism by introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene. The term "autologous gene" is intended to encompass variants (e.g., polymorphisms or mutants) of the naturally occurring gene. The term transgene thus encompasses the replacement of the naturally occurring gene with a variant form of the gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes.

The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der E b (Graham and van der E b, Virol., 52:456 [1973]), has been modified by several groups to optimize conditions for particular types of cells. The art is well aware of these numerous modifications.

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. As used herein, the term "sample" is used in its broadest sense. In one sense it can refer to a tissue sample. In another sense, it is meant to include a specimen or culture obtained from any source, as well as biological. Biological samples may be obtained from animals (including humans) and encompass fluids, solids, tissues, and gases. Biological samples include, but are not limited to blood products, such as plasma, serum and the like. These examples are not to be construed as limiting the sample types applicable to the present invention. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "response," when used in reference to an assay, refers to the generation of a detectable signal (e.g., accumulation of reporter protein, increase in ion concentration, accumulation of a detectable chemical product).

As used herein, the term "membrane receptor protein" refers to membrane spanning proteins that bind a ligand (e.g., a hormone or neurotransmitter). As is known in the art, protein phosphorylation is a common regulatory mechanism used by cells to selectively modify proteins carrying regulatory signals from outside the cell to the nucleus. The proteins that execute these biochemical modifications are a group of enzymes known as protein kinases. They may further be defined by the substrate residue that they target for phosphorylation. One group of protein kinases are the tyrosine kinases (TKs) which selectively phosphorylate a target protein on its tyrosine residues. Some tyrosine kinases are membrane-bound receptors (RTKs), and, upon activation by a ligand, can autophosphorylate as well as modify substrates. The initiation of sequential phosphorylation by ligand stimulation is a paradigm that underlies the action of such effectors as, for example, epidermal growth factor (EGF), insulin, platelet-derived growth factor (PDGF), and fibroblast growth factor (FGF). The receptors for these ligands are tyrosine kinases and provide the interface between the binding of a ligand (hormone, growth factor) to a target cell and the transmission of a signal into the cell by the activation of one or more biochemical pathways. Ligand binding to a receptor tyrosine kinase activates its intrinsic enzymatic activity. Tyrosine kinases can also be cytoplasmic, non-receptor-type enzymes and act as a downstream component of a signal transduction pathway.

As used herein, the term "signal transduction protein" refers to proteins that are activated or otherwise effected by ligand binding to a membrane receptor protein or some other stimulus. Examples of signal transduction protein include adenyl cyclase, phospholipase C, and G-proteins. Many membrane receptor proteins are coupled to G-proteins (i.e., G-protein coupled receptors (GPCRs); for a review, see Neer, 1995, Cell 80:249–257 [1995]). Typically, GPCRs contain seven transmembrane domains. Putative GPCRs can be identified on the basis of sequence homology to known GPCRs.

As used herein, the term "nucleic acid binding protein" refers to proteins that bind to nucleic acid, and in particular to proteins that cause increased (i.e., activators or transcription factors) or decreased (i.e., inhibitors) transcription from a gene.

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos. 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

As used herein, the term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

DETAILED DESCRIPTION OF THE INVENTION

The present invention relates to intracellular signaling molecules, in particular the Nod1 protein. The present invention provides methods of identifying modulators of Nod1 signaling. The present invention further provides methods of altering Nod1 signaling. The below description provides non-limiting examples of drug screening and therapeutic applications of altering Nod1 signaling. One skilled in the relevant art recognizes that other applications are within the scope of the present invention.

I. Generation of Nod1 Antibodies

Antibodies can be generated to allow for the detection of Nod1 protein (e.g., in drug screening embodiments of the present invention described below). The antibodies may be prepared using various immunogens. In one embodiment, the immunogen is a human Nod1 peptide to generate antibodies that recognize human Nod1. Such antibodies include, but are not limited to polyclonal, monoclonal, chimeric, single chain, Fab fragments, and Fab expression libraries.

Various procedures known in the art may be used for the production of polyclonal antibodies directed against Nod1. For the production of antibody, various host animals can be immunized by injection with the peptide corresponding to the Nod1 epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward Nod1, it is contemplated that any technique that provides for the production of antibody molecules by continuous cell lines in culture will find use with the present invention (See e.g., Harlow and Lane, *Antibodies: A Laboratory Manual, Cold Spring Harbor Laboratory Press*, Cold Spring Harbor, N.Y.). These include but are not limited to the hybridoma technique originally developed by Köhler and Milstein (Köhler and Milstein, Nature 256:495–497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in *Monoclonal Antibodies and Cancer Therapy*, Alan R. Liss, Inc., pp. 77–96 [1985]).

In an additional embodiment of the invention, monoclonal antibodies are produced in germ-free animals utilizing technology such as that described in PCT/US90/02545). Furthermore, it is contemplated that human antibodies will be generated by human hybridomas (Cote et al., Proc. Natl. Acad. Sci. USA 80:2026–2030 [1983]) or by transforming human B cells with EBV virus in vitro (Cole et al., in *Monoclonal Antibodies and Cancer Therapy*, Alan R. Liss, pp. 77–96 [1985]).

In addition, it is contemplated that techniques described for the production of single chain antibodies (U.S. Pat. No. 4,946,778; herein incorporated by reference) will find use in producing Nod1 specific single chain antibodies. An additional embodiment of the invention utilizes the techniques described for the construction of Fab expression libraries (Huse et al., Science 246:1275–1281 [1989]) to allow rapid and easy identification of monoclonal Fab fragments with the desired specificity for Nod1. In some embodiments, humanized antibodies are generated (See e.g., U.S. Pat. Nos. 6,180,370, 5,585,089, 6,054,297, and 5,565,332; each of which is herein incorporated by reference).

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. (As is well known in the art, the immunogenic peptide should be provided free of the carrier molecule used in any immunization protocol. For example, if the peptide was conjugated to KLH, it may be conjugated to BSA, or used directly, in a screening assay).

The foregoing antibodies can be used in methods known in the art relating to the localization and structure of Nod1 (e.g., for Western blotting), measuring levels thereof in appropriate biological samples, etc. The antibodies can be used to detect Nod1 in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of human Nod1 using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of Nod1 detected by immunoblotting (Western blotting). Immunoblotting techniques are generally more effective with antibodies generated against a peptide corresponding to an epitope of a protein, and hence, are particularly suited to the present invention.

Another method uses antibodies as agents to alter signal transduction. Specific antibodies that bind to the binding domains of Nod1 or other proteins involved in intracellular signaling can be used to inhibit the interaction between the various proteins and their interaction with other ligands. Antibodies that bind to the complex can also be used therapeutically to inhibit interactions of the protein complex in the signal transduction pathways leading to the various physiological and cellular effects of NF-κB. Such antibodies can also be used diagnostically to measure abnormal expression of Nod1, or the aberrant formation of protein complexes, which may be indicative of a disease state.

II. Transgenic Animals Expressing Exogenous Nod1 Genes and Homologs, Mutants, and Variants Thereof The present invention contemplates the generation of transgenic animals comprising an exogenous Nod1 gene or homologs, mutants, or variants thereof. In preferred embodiments, the transgenic animal displays an altered phenotype as compared to wild-type animals. In some embodiments, the altered phenotype is the overexpression of mRNA for a Nod1 gene as compared to wild-type levels of Nod1 expression. In other embodiments, the altered phenotype is the decreased expression of mRNA for an endogenous Nod1 gene as compared to wild-type levels of endogenous Nod1 expression. Methods for analyzing the presence or absence of such phenotypes include Northern blotting, mRNA protection assays, and RT-PCR. In other embodiments, the transgenic mice have a knock out mutation of the Nod1 gene. In still further embodiments, the transgenic animal comprises a variant Nod1 gene. In preferred embodiments, the transgenic animals display a disease phenotype (e.g., an inflammatory disease).

The transgenic animals of the present invention find use in dietary and drug screens. In some embodiments, the transgenic animals (e.g., animals displaying a Crohn's disease or asthma phenotype) are fed test or control diets and the response of the animals to the diets is evaluated. In other embodiments, test compounds (e.g., a drug that is suspected of being useful to treat inflammatory disease) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter, which allows reproducible injection of 1–2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438–4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260–1264 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad. Sci. USA 82:6927–693 [1985]). Transfection is easily and efficiently obtained by culturing the blastomeres on a monolayer of virus-producing cells (Van der Putten, supra; Stewart, et al., EMBO J., 6:383–388 [1987]). Alternatively, infection can be performed at a later stage. Virus or virus-producing cells can be injected into the blastocoele (Jahner et al., Nature 298:623–628 [1982]). Most of the founders will be mosaic for the transgene since incorporation occurs only in a subset of cells that form the transgenic animal. Further, the founder may contain various retroviral insertions of the transgene at different positions in the genome, which generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involves the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154–156 [1981]; Bradley et al., Nature 309:255–258 [1984]; Gossler et al., Proc. Acad. Sci. USA 83:9065–9069 [1986]; and Robertson et al., Nature 322:445–448 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468–1474 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants. Methods for homologous recombination are described in U.S. Pat. No. 5,614,396, incorporated herein by reference.

III. Nod1 Ligands

As described herein, experiments conducted during the course of development of the present invention resulted in the identification of Nod1 ligands. Such ligands find use a variety of applications, including, but not limited to, the drug screening and therapeutic applications described below.

A. Ligands

Experiments conducted during the course of development of the present invention identified two dipeptides, glutamic acid-diaminopimelic acid and glutamine-diaminopimelic acid, as minimal ligands for Nod1. In particular, γ-D-glutamy-meso-diaminopimelic acid (iE-DAP) and γ-D-Gln-DAP (iQ-DAP) were identified as dipeptides that stimulated Nod1 activity. However, the present invention is not limited to these particular peptides. It is contemplated that other peptides comprising iE-DAP and iQ-DAP are suitable as ligands of Nod1. Potential ligands can be screened using any suitable method including, but not limited to, the screening methods disclosed herein.

B. Mimetics

The present invention is not limited to peptide ligands of Nod1. In still further embodiments, the present invention contemplates compounds mimicking the necessary conformation for recognition and/or docking to the receptor binding to the peptides of the present invention. A variety of designs for such mimetics are possible. For example, cyclic-containing peptides, in which the necessary conformation for binding is stabilized by nonpeptides, are specifically contemplated. U.S. Pat. No. 5,192,746, U.S. Pat. No. 5,169,862, U.S. Pat. No. 5,539,085, U.S. Pat. No. 5,576,423, U.S. Pat. No. 5,051,448, and U.S. Pat. No. 5,559,103, all hereby incorporated by reference, describe multiple methods for creating such compounds.

Synthesis of nonpeptide compounds that mimic peptide sequences is also known in the art. Eldred et al. (J. Med. Chem., 37:3882 [1994]) describe nonpeptide antagonists that mimic the peptide sequences. Likewise, Ku et al. (J. Med. Chem., 38:9 [1995]) give further elucidation of the synthesis of a series of such compounds. Such nonpeptide compounds that mimic peptide inhibitors of the present invention are specifically contemplated by the present invention.

The present invention also contemplates synthetic mimicking compounds that are multimeric compounds that repeat the relevant peptide sequence. As is known in the art, peptides can be synthesized by linking an amino group to a carboxyl group that has been activated by reaction with a coupling agent, such as dicyclohexylcarbodiimide (DCC). The attack of a free amino group on the activated carboxyl leads to the formation of a peptide bond and the release of dicyclohexylurea. It can be necessary to protect potentially reactive groups other than the amino and carboxyl groups intended to react. For example, the α-amino group of the component containing the activated carboxyl group can be blocked with a tertbutyloxycarbonyl group. This protecting group can be subsequently removed by exposing the peptide to dilute acid, which leaves peptide bonds intact.

With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary.

In one embodiment, the mimetics of the present invention are peptides having sequence homology to the peptides described herein. One common methodology for evaluating sequence homology, and more importantly statistically significant similarities, is to use a Monte Carlo analysis using an algorithm written by Lipman and Pearson to obtain a Z value. According to this analysis, a Z value greater than 6 indicates probable significance, and a Z value greater than 10 is considered to be statistically significant (Pearson and Lipman, Proc. Natl. Acad. Sci. (USA), 85:2444–2448 (1988); Lipman and Pearson, Science, 227:1435 (1985)). In the present invention, synthetic polypeptides useful as modulators of Nod1 signaling are those peptides with statistically significant sequence homology and similarity (Z value of Lipman and Pearson algorithm in Monte Carlo analysis exceeding 6).

In some particularly preferred embodiments, mimetic compounds are those in which the peptide cycle is replaced by any non-peptide scaffold that allows comparable positioning of functional equivalents of the peptides of the present invention.

C. Other Modified Peptides

The present invention further includes peptides modified to improve one or more properties useful in pharmaceutical compounds. For example, in some embodiments, peptides are modified to enhance their ability to enter intracellular space. Such modifications include, but are not limited to, the addition of charged groups, lipids and myristate groups (See e.g., U.S. Pat. No. 5,607,691; herein incorporated by reference).

In other embodiments, the peptides of the present invention may be in the form of a liposome in which isolated peptide is combined, in addition to other pharmaceutically acceptable carriers, with amphipathic agents such as lipids which exist in aggregated form as micelles, insoluble monolayers, liquid crystals, or lamellar layers which exist in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

IV. Drug Screening Using Nod1

The present invention provides methods and compositions for using Nod1 as a target for screening drugs that can alter, for example, RICK signaling, and thus the physiological effects of NF-κB (e.g., inflammatory response). For example, drugs that induce or inhibit NF-κB mediated inflammatory responses can be identified by screening for compounds that target Nod1 or regulate Nod1 gene expression. In other embodiments, drug screening assays identify ligands or modulators of Nod1 signaling for use in the treatment of inflammatory disease (e.g., Crohn's disease or asthma).

As described above, experiments conducted during the course of development of the present invention demonstrated that Nod1 is involved in recognition of bacterial peptidoglycans containing diaminopimelic acid (DAP, e.g., iE-DAP or iQ-DAP). Accordingly, in some embodiments, the present invention provides methods of screening for compounds that alter (e.g., enhance or inhibit) this response. For example, in some embodiments, an NF-κB reporter gene assay (See e.g., Experimental Section) or other NF-κB activation assay is used to screen for compounds that alter the host response to iE-DAP, iQ-DAP or mimetics or analogs thereof. In some embodiments, a mutant Nod1 that does not respond to iE-DAP or iQ-DAP is expressed in cells and libraries of compounds are screened for their ability to restore the NF-κB activation response. In some embodiments, the test compounds are analogs and derivatives of iE-DAP or iQ-DAP.

In other embodiments, the present invention provides methods of screening compounds (e.g., iE-DAP, iQ-DAP or analogs or mimetics thereof) for the ability to induce Nod1 mediated NF-κB activation. As described above, such compounds find use in the treatment of inflammatory diseases (e.g., asthma or Crohn's disease). In other embodiments, the present invention provides methods of screening for compounds (e.g., iE-DAP or iQ-DAP analogs and mimetics) that inhibit Nod1 mediated NF-κB activation. For example, in some embodiments, compounds are contacted with a cell expressing wild type Nod1 and the activation of NF-κB is measured (e.g., using the reporter gene assay described in the below Examples). In some embodiments, the level of NF-κB is compared to the level of NF-κB activation induced by iE-DAP or iQ-DAP analogs or other test compounds.

The present invention is not limited to iE-DAP or iQ-DAP-based test compounds. Additional test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678–85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412–421 [1992]), or on beads (Lam, Nature 354:82–84 [1991]), chips (Fodor, Nature 364:555–556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386–390 [1990]; Devlin Science 249:404–406 [1990]; Cwirla et al., Proc. Natl. Acad. Sci. 87:6378–6382 [1990]; Felici, J. Mol. Biol. 222:301 [1991]).

In other embodiments, drug screens are used to identify compounds that alter the ability of Nod1 to interact with binding partners. It is contemplated that binding assays are useful for screening for compounds that block or enhance Nod1 binding to Nod1 binding partners. The binding need not employ full-length Nod1 binding partner and Nod1. Indeed, portions of Nod1 binding partner and Nod1 may be utilized in the binding assays. For example, in some embodiments, a fragment of Nod1 containing CARD domains is utilized in the binding assay.

In other embodiments, the present invention provides methods of screening for compounds that increase or decrease the recognition or binding of Nod1 to pathogens, pathogen components, or pathogen binding proteins, and consequently, affect downstream signaling and NF-κB activation. In some embodiments, wild-type Nod1 or a fragment thereof is utilized. In other embodiments, Nod1 containing one or more variations (e.g., mutations or polymorphisms) is utilized.

In one screening method, the two-hybrid system is used to screen for compounds capable of altering (e.g., enhancing or inhibiting) Nod1 function(s) (e.g., NF-κB-mediated signal transduction) in vitro or in vivo. In one embodiment, a GAL4 binding site, linked to a reporter gene such as lacZ, is contacted in the presence and absence of a candidate compound with a GAL4 binding domain linked to a Nod1 fragment and a GAL4 transactivation domain II linked to a NF-κB fragment. Expression of the reporter gene is monitored and a decrease in the expression is an indication that the candidate compound inhibits the interaction of Nod1 with NF-κB. Alternately, the effect of candidate compounds on the interaction of Nod1 with other proteins (e.g., proteins known to interact directly or indirectly with NF-κB) can be tested in a similar manner.

In another screening method, candidate compounds are evaluated for their ability to alter Nod1 signaling by contacting Nod1, NF-κB, NF-κB-associated proteins, or fragments thereof, with the candidate compound and determining binding of the candidate compound to the peptide. The protein or protein fragments is/are immobilized using methods known in the art such as binding a GST-Nod1 fusion protein to a polymeric bead containing glutathione. A chimeric gene encoding a GST fusion protein is constructed by fusing DNA encoding the polypeptide or polypeptide fragment of interest to the DNA encoding the carboxyl terminus of GST (See e.g., Smith et al., Gene 67:31 [1988]). The fusion construct is then transformed into a suitable expression system (e.g., E. coli XA90) in which the expression of the GST fusion protein can be induced with isopropyl-β-D-thiogalactopyranoside (IPTG). Induction with IPTG should yield the fusion protein as a major constituent of soluble, cellular proteins. The fusion proteins can be purified by methods known to those skilled in the art, including purification by glutathione affinity chromatography. Binding of the candidate compound to the proteins or protein fragments is correlated with the ability of the compound to disrupt the signal transduction pathway and thus regulate Nod1 physiological effects (e.g., inflammatory disease).

In another screening method, one of the components of the Nod1/NF-κB signaling system, such as Nod1 or a fragment of Nod1, is immobilized. Polypeptides can be immobilized using methods known in the art, such as adsorption onto a plastic microtiter plate or specific binding of a GST-fusion protein to a polymeric bead containing glutathione. For example, GST-Nod1 is bound to glutathione-Sepharose beads. The immobilized peptide is then contacted with another peptide with which it is capable of binding in the presence and absence of a candidate compound. Unbound peptide is then removed and the complex solubilized and analyzed to determine the amount of bound labeled peptide. A decrease in binding is an indication that the candidate compound inhibits the interaction of Nod1 with the other peptide. A variation of this method allows for the screening of compounds that are capable of disrupting a previously-formed protein/protein complex. For example, in some embodiments a complex comprising Nod1 or a Nod1 fragment bound to another peptide is immobilized as described above and contacted with a candidate compound. The dissolution of the complex by the candidate compound correlates with the ability of the compound to disrupt or inhibit the interaction between Nod1 and the other peptide.

Another technique for drug screening provides high throughput screening for compounds having suitable binding affinity to Nod1 peptides and is described in detail in WO 84/03564, incorporated herein by reference. Briefly, large numbers of different small peptide test compounds are synthesized on a solid substrate, such as plastic pins or some other surface. The peptide test compounds are then reacted with Nod1 peptides and washed. Bound Nod1 peptides are then detected by methods well known in the art.

Another technique uses Nod1 antibodies, generated as discussed above. Such antibodies capable of specifically binding to Nod1 peptides compete with a test compound for binding to Nod1. In this manner, the antibodies can be used to detect the presence of any peptide that shares one or more antigenic determinants of the Nod1 peptide.

In some embodiments of the present invention, compounds are screened for their ability to inhibit the binding of pathogen components (e.g., including, but not limited to, bacterial cell surface proteins; fungi proteins, parasite proteins, and virus proteins) to Nod1. Any suitable screening assay may be utilized, including, but not limited to, those described herein.

The present invention contemplates many other means of screening compounds. The examples provided above are presented merely to illustrate a range of techniques available. One of ordinary skill in the art will appreciate that many other screening methods can be used.

In particular, the present invention contemplates the use of cell lines transfected with Nod1 and variants thereof for screening compounds for activity, and in particular to high throughput screening of compounds from combinatorial libraries (e.g., libraries containing greater than $10^4$ compounds). In some embodiments, the libraries are libraries of iE-DAP or iQ-DAP analogs. The cell lines of the present invention can be used in a variety of screening methods. In some embodiments, the cells can be used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, the host cells are preferably transfected as described above with vectors encoding Nod1 or variants or mutants thereof. The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, IP3, cAMP, arachidonic acid release) due to stimulation of membrane receptors and ion channels (e.g., ligand gated ion channels; see Denyer et al., Drug Discov. Today 3:323 [1998]; and Gonzales et al., Drug. Discov. Today 4:431–39 [1999]). Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the host cells are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75 [1996]), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The cells are also useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product. In some embodiments, the reporter gene construct comprises the 5' regulatory region (e.g., promoters and/or enhancers) of a protein whose expression is controlled by NF-κB in operable association with a reporter gene (See Examples below and Inohara et al., J. Biol. Chem. 275:27823 [2000] for a description of the luciferase reporter construct pBVIx-Luc). Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluminescent, calorimetric, or bioluminecent products of specific substrates (e.g., X-gal and luciferin). Comparisons between compounds of known and unknown activities may be conducted as described above.

V. Therapeutics

In still further embodiments, the present invention provides therapeutics useful in the treatment of inflammatory (e.g., asthma and Crohn's disease). As described elsewhere, patients with mutations in Nod2 lack a response or have a diminished response to bacterial muropeptides. As described above, it is contemplated that stimulation of Nod1 signaling may be used to compensate for defective Nod2 signaling in Crohn's disease. Accordingly, it is contemplated that iE-DAP, iQ-DAP or mimetics or analogs thereof find use in the treatment of Crohn's disease. In some embodiments, therapeutics are identified using the drug screening methods described above.

In some embodiments, therapeutics (e.g., Crohn's disease therapeutics) are delivered to the gut. In other embodiments, therapeutics are delivered to the blood. Exemplary formulation and delivery methods are described below.

In other embodiments, the present invention provides compounds (e.g., iE-DAP, iQ-DAP or analogs or mimetics therof) that alter (e.g., increase or decrease) Nod1 signaling. Such compounds find use in the modulation of Nod1 signaling (e.g., compounds that increase or decrease Nod1 signaling).

VI. Pharmaceutical Compositions Containing Nod1 Analogs and Modulators

The present invention further provides pharmaceutical compositions which may comprise all or portions of Nod1 ligands, inhibitors, activators or antagonists of Nod1 bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, Nod1 modulators or ligands can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of a compound of the present invention may be that amount that suppresses symptoms of an inflammatory disease. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

In some embodiments, drug delivery systems are used that deliver the pharmaceutical compound of interest (e.g., iE-DAP, iQ-DAP or analogs thereof) directly to the gut. Several types of colonic drug delivery systems are currently available, including enemas (Sutherland et al., Med. Clin. North Amer., 74, 119 (1990)); rectal foams (Drug. Ther. Bull., 29, 66 (1991)); and delayed release oral formulations in the form of Eudragit-coated capsules which dissolve at pH 7 in the terminal ileum (Schroeder et al., New Engl. J. Med., 317, 1625 (1987)). In other embodiments enteric coatings, which remain undissociated in the low pH environment of the stomach, but readily ionize when the pH rises to about 4 or 5 are utilized, including, but not limited to, polyacids having a pHa of 3 to 5.

Compositions comprising a compound of the invention formulated in a pharmaceutical acceptable carrier may be prepared, placed in an appropriate container, and labeled for treatment of an indicated condition. For polynucleotide or amino acid sequences of Nod1, conditions indicated on the label may include treatment of conditions related to inflammation.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts levels of the pharmaceutical of interest.

A therapeutically effective dose refers to that amount of a compound of the present invention that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference). Those skilled in the art may employ different formulations for activators of Nod1 than for the inhibitors of Nod1. Administration to the bone marrow may necessitate delivery in a manner different from intravenous injections.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); µg (micrograms); ng (nanograms); l or L (liters); ml (milliliters); µl (microliters); cm (centimeters); mm (millimeters); µm (micrometers); nm (nanometers); ° C. (degrees Centigrade); U (units), mU (milliunits); min. (minutes); sec. (seconds); % (percent); kb (kilobase); bp (base pair); PCR (polymerase chain reaction); BSA (bovine serum albumin).

Example 1

Materials and Methods

Reagents. LPS from *S. typhimurium*, intact and alkaline-detoxified LPS from *E. coli* O55:B5 as well as purified lipid A preparations of *E. coli* F583, MDP, DAP and dsRNA were obtained from Sigma-Aldrich (St. Louis, Mo.). PGN from *S. aureus* was from Fluka-Chemie (Buchs, Germany). Palmitoyl-Cys ((RS)-2,3-di(palmitoyloxy)-propyl)-Ala-Gly) (sBLP), was obtained from Bachem (Torrance, Calif.). The tetrameric form of the disaccharide dipeptide was described previously (Inohara et al., J. Biol. Chem. 278:5509 [2003]). iE-DAP and iQ-DAP, M3P and M4P were synthesized as described (Kitaura et al., J. Med. Chem. 25:335 [1982]) with small modification. Purification of PGN from *B. subtilis* 168 and *C. flaccumfaciens* with hydrolases, Cellosyl or recombinant AtlE (amidase domain) and the fractionation and purification of reduced *B. subtilis* PGN digested with Cellosyl were performed as previously described (Heilman et al., Mol. Microbiol. 24:1013 [1997]; Atrih et al., J. Bact. 181:3956 [1999]).

Removal of proteins and reduction of LPS fraction. *E. coli* O55:B5 LPS (Sigma) was treated with proteinase K at 37° C. for 12 hr to digest contaminating proteins. To eliminate lipoproteins, LPS was subjected to modified phenol extraction with deoxycholate-containing phenol as described (Hirschfeld et al., J. Immunol. 165:618 [2000]). For reduction of carboxyl group in the LPS, the LPS was treated with 1-ethyl-3-(3-dimethylaminopropyl) carbodiimide and then reduced with $NaBH_4$ as described (Taylor et al., Biochemistry 11:1383 [1972]).

Preparation of *E. coli* extract. *E. coli* K-12 mutants were all based on the SØ864 genetic background (lacZ trp upp relA rpsL) (Neuhard and Thomassen, J. Bacteriol. 126:999). SØ874 carries a large chromosomal deletion removing the gene clusters for the biosynthesis of CA capsule and O-antigen. CLM5 is a derivative of SØ874 with a transposon insertion in the wecC gene that blocks the synthesis of ECA (Marolda et al., J. Bacteriol. 177:5539[1995]). FAM5 is a derivative of SØ874 carrying a deletion that eliminates the incorporation of heptose in the LPS core. Extracts were prepared from all of these *E. coli* K-12 strains and also from another *E. coli* K-12 strain, LCD27 YA21-6 (Obtained from Dr. Arisaka, Tokyo Institute of Technology). Bacteria were cultured overnight at 37° C. in Luria broth, killed by treatment with acetone followed by vacuum drying and finally resuspended in 10 mM HEPES. The extract was treated with 1M NaOH at 55° C. for 12 hr and neutralized with 1M HEPES (pH 7.4). The soluble fraction after centrifugation and filtration with 0.22 µm filter was applied to SUPEROSE 12 gel filtration column chromatography.

Partial purification of NOD1-stimulatory molecules from *E. coli* and composition analyses. The amino acid composition of *E. coli* O55:B5 LPS was determined using AccQ·Tag amino acid analysis system (Waters, Milford, Mass.) after hydrolysis at 110° C. for 24 hr. For carbohydrate analysis, *E. coli* K-12 YA21-6 (Ref 26) cultured overnight at 37° C. in L-broth were washed with TBS twice and incubated with TBS containing 1 mglml DNase I, RNase I and lysozyme for 37° C. for 2 hr. Acetone was added to the extracts at 50% final concentration and the insoluble fractions were washed with an excess of 75% and 100% acetone. After vacuum drying, the acetone extract was solublized with 1 M NaOH and incubated at 60° C. for 24 hr. The pH was adjusted to pH 5.0 with acetic acid and the soluble fraction was passed through SUPEROSE gel filtration column. SUPEROSE fractions with NOD1-stimulatory activity were diluted with 10 mM Tris-HCl (pH 8.8) and subjected to UnoQ column chromatography. The fractions were eluted with a linear gradient of 0–300 mM NaCl. The positive fractions were dialyzed against water and dried under vacuum. The monosaccharide composition of the fractions after TFA/methanol degradation was determined as previously described (Forsberg et al., J. Biol. Chem. 273:2747[1998]).

Transfection and NF-κB Activation Assay. Plasmids pcDNA3-NOD1-FLAG, pcDNA3-NOD1-ΔLRR(1–648)-FLAG, pcDNA3-NOD2, pcDNA3-TLR4 and pcDNA3-MD2, pDisplay-HA-TLR1, pDisplay-HA-TLR1TLR6 have been previously described (Inohara et al., J. Biol. Chem. 274:14560 [1999]; Inohara et al., J. Biol. Chem. 278:5509 [2003]). Transfection of plasmids and NF-κB activation assays with HEK293T cells were performed as described (Inohara et al., J. Biol. Chem. 274:14560 [1999]). LPS, PGN and MDP derivatives were added to the cultures as reported (Inohara et al., J. Biol. Chem. 276:2551 [2001]). Results were normalized for transfection efficiency with values obtained with pEF-BOS-β-gal.

Generation of NOD1 deficient mice. Mutant mice deficient in NOD1 were generated by homologous recombination using a targeting construct designed to replace the first and second coding exons of nod1 with a neomycin (neo) resistant cassette. 129/C57B1/6 chimaeric mice were crossed with C57B16 females to generate Nod1 +/- mice. The genotype of mice was determined by Southern blot analysis and subsequent screening was performed by PCR analysis using primers specific to neo-targeted and wild type nod1 alleles. nod1 +/+ and nod1 -/- littermate mice from C57B1/6×129 F4-5 background were used. The expression status of the nod1 gene was assessed by semi-quantitative RT-PCR on liver-derived total RNA samples from nod1 -/- and wild-type littermates.

Cytokine Secretion Assays. Macrophages were derived from bone marrow as described (Kobayashi et al., supra). Cells were harvested with cold DPBS, washed, resuspended in DMEM supplemented with 10% fetal calf serum and used at a density of $3 \times 10^5$/ml. Bone marrow-derived macrophages were cultured with the indicated concentration of iE-DAP, MDP or dsRNA for 12 hr. The concentration of IL-6 and TNF-α in culture supernatants was measured by ELISA.

Example 2

NOD1-Stimulatory Molecules are Different from Bacterial Lipopolysaccharide

Previous studies showed that NOD1 can mediate MyD88-independent cellular responsiveness to LPS preparations from various Gram-negative bacteria including *Escherichia coli*, but not to PGN from the Gram-positive bacterium *Staphylococcus aureus* (Inohara et al., J. Biol. Chem. 276: 2551[2001]). To further characterize the bacterial moiety detected by NOD1, human embryonic kidney (HEK293T) cells harboring a NF-κB-dependent luciferase reporter were used and the ability of NOD1, NOD2 and TLR4 to recognize LPS and PGN was compared. Expression of NOD1, NOD2 or TLR4 together with its co-factor MD-2 conferred responsiveness to commercial LPS preparation from *E. coli* O55:B5 that was purified by phenol-water extraction, whereas only NOD2 induced the response to *S. aureus* PGN (FIG. 1a). The lipid A moiety of LPS is implicated in TLR4/MD-2 activation. NOD1 and NOD2, but not TLR4, mediated a response to detoxified LPS containing deacylated lipid A that was prepared by alkaline treatment (FIG. 1a). TLR4, but not NOD1 and NOD2, responded to purified intact lipid A (FIG. 1a). These results indicate that NOD1, NOD2 and TLR4 recognize different bacterial components. To further characterize the component recognized by NOD1, purified LPS were fractionated by SUPEROSE gel filtration column chromatography and the fractions were tested for NOD1- and TLR4-stimulatory activities. Whereas a TLR4-mediated response was stimulated by high molecular weight fractions consistent with the expected chromatographic profile of LPS, the NOD1-stimulatory activity was detected only in fractions smaller than 12 kDa (FIG. 1b).

Since only the TLR4-stimulatory activity was abrogated by the deacylated lipid A preparation (FIG. 1a) and NOD1 did not respond to intact lipid A, these results suggest that the NOD1 stimulatory component is not lipid A, and probably represents a breakdown product of the LPS molecule or a biologically active contaminant in the LPS preparation. Structurally, the *E. coli* O55:B5 LPS consists of an O-antigen polysaccharide, composed of repeating oligosaccharide subunits, that is linked to a core oligosaccharide-lipid A region which serves to anchor the LPS to the bacterial outer membrane (Raetz et al., Ann. Rev. Biochem. 71:635 [2002]). To determine whether carbohydrate components of the O-antigen and core regions of LPS are involved in NOD1 signaling, whole-cell extracts were prepared from *E. coli* K-12 mutants (i.e. lacking enzymes that are required for the synthesis of O-antigen). Mutants defective in the synthesis of the majority of the core oligosaccharide, resulting in the production of a heptoseless LPS, were also analyzed (Raetz et al., supra; Valvano et al., Microbiology 148:1979 [2002]). In addition, extracts from *E. coli* mutants that lack colanic acid (CA) capsule and enterobacterial common antigen (ECA) were tested, as these carbohydrate structures could potentially contaminate LPS preparations. For consistency, all of these mutants were constructed in the same genetic background of the *E. coli* K-12 strain SØ864, which does not produce an O-antigen. LPS extracts from parental and mutant strains were fractionated by gel filtration and systematically the fractions were assessed for their ability to stimulate NOD1. All of these extracts induced NOD1-dependent NF-κB activation in HEK293T cells (FIG. 1c). The size profile of NOD1-stimulatory fractions was identical in all preparations and also corresponded to fractions smaller than 12 kDa in mass (FIG. 1c). These results indicate that carbohydrates such as those present in the O-antigen, core oligosaccharide, ECA and CA capsule are not required for stimulation of NOD1.

Example 3

DAP-Type Peptidoglycan Induces NOD1-Mediated NF-κB Activation

Previous studies revealed that certain LPS preparations are contaminated with bacterial lipoproteins that can result in the stimulation of TLR2 (Hirschfeld et al., J. Immunol. 165:618 [2000]). To investigate whether the active LPS preparation contained lipoproteins, the amino acid composition of the LPS fraction capable of stimulating NOD1 was determined. This analysis revealed that the active fraction contained detectable amino acids including diaminopimelic acid (DAP), an unique amino acid present in PGN (FIG. 2a). This result indicates that the active fraction contains both bacterial proteins and PGN. The partially purified NOD1-stimulatory component bound to UnoQ ionic exchange resin, suggesting that it contains negative charges. Treatment of the LPS fraction with the reducing agent $NaBH_4$ abrogated the NOD1-stimulatory activity (FIG. 2b), suggesting that the active component may contain carboxyl residues such as those present in amino acid residues present in bacterial proteins and PGN. To test whether bacterial proteins are important for NOD1-stimulatory activity, the active LPS preparation was subjected to several treatments that inactivate or remove proteinaceous components. The NOD1-stimulatory activity was resistant to various protein extraction methods including modified phenol extraction (FIG. 2b) and proteinase K digestion, suggesting that it was neither a conventional polypeptide nor a lipoprotein. Furthermore, the NOD1-stimulatory activity was resistant to alkaline and acid treatment that is expected to hydrolyze most proteins (FIG. 2b), whereas the TLR4-stimulatory activity present in the LPS preparation was highly sensitive to the same treatment.

Figure 2:
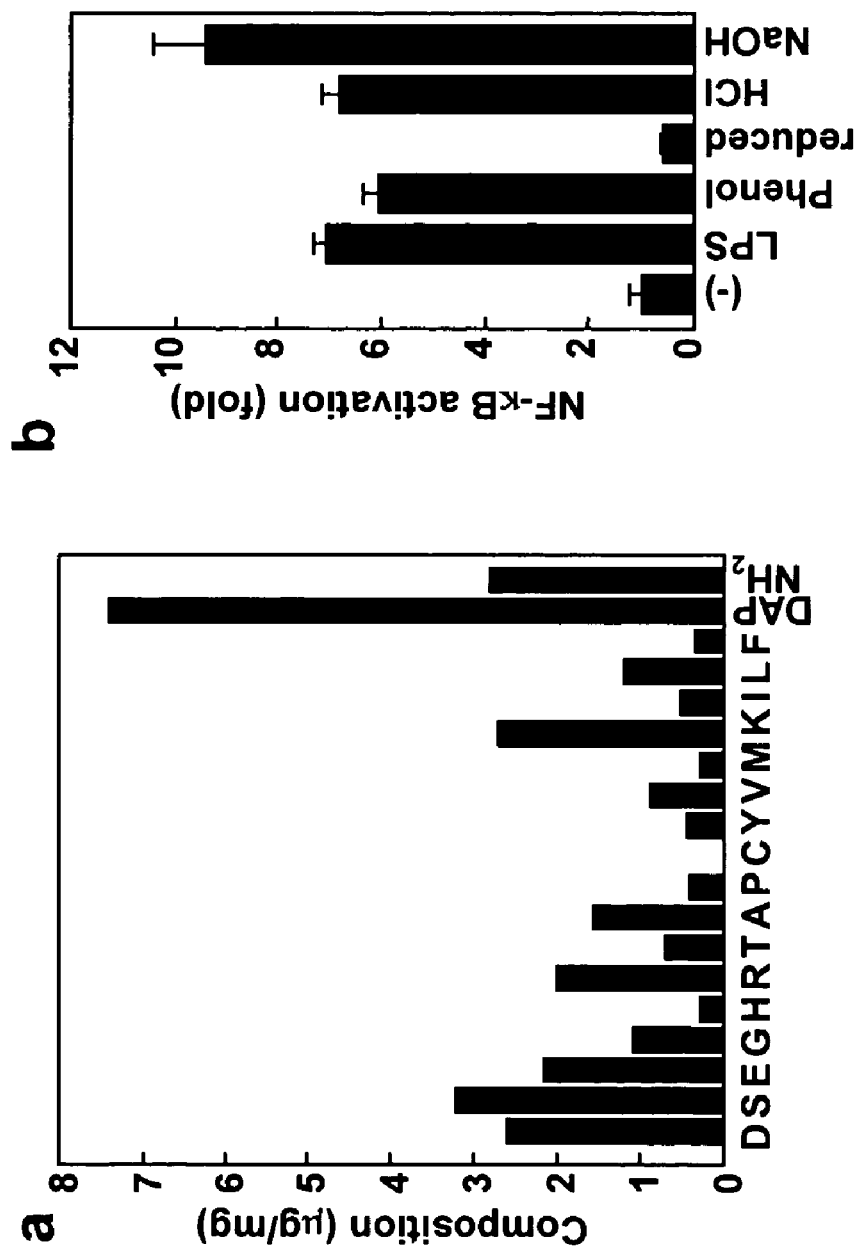
FIG. 2 shows that the NOD1-stimulatory fraction in LPS preparation contains DAP-type Peptidoglycan. A) Amino acid composition of the LPS preparation. B) Reporter gene assay of Nod1 stimulated with LPS preparations. The transcriptional activity in the absence of the ligand is given as 1.
Figure 3:
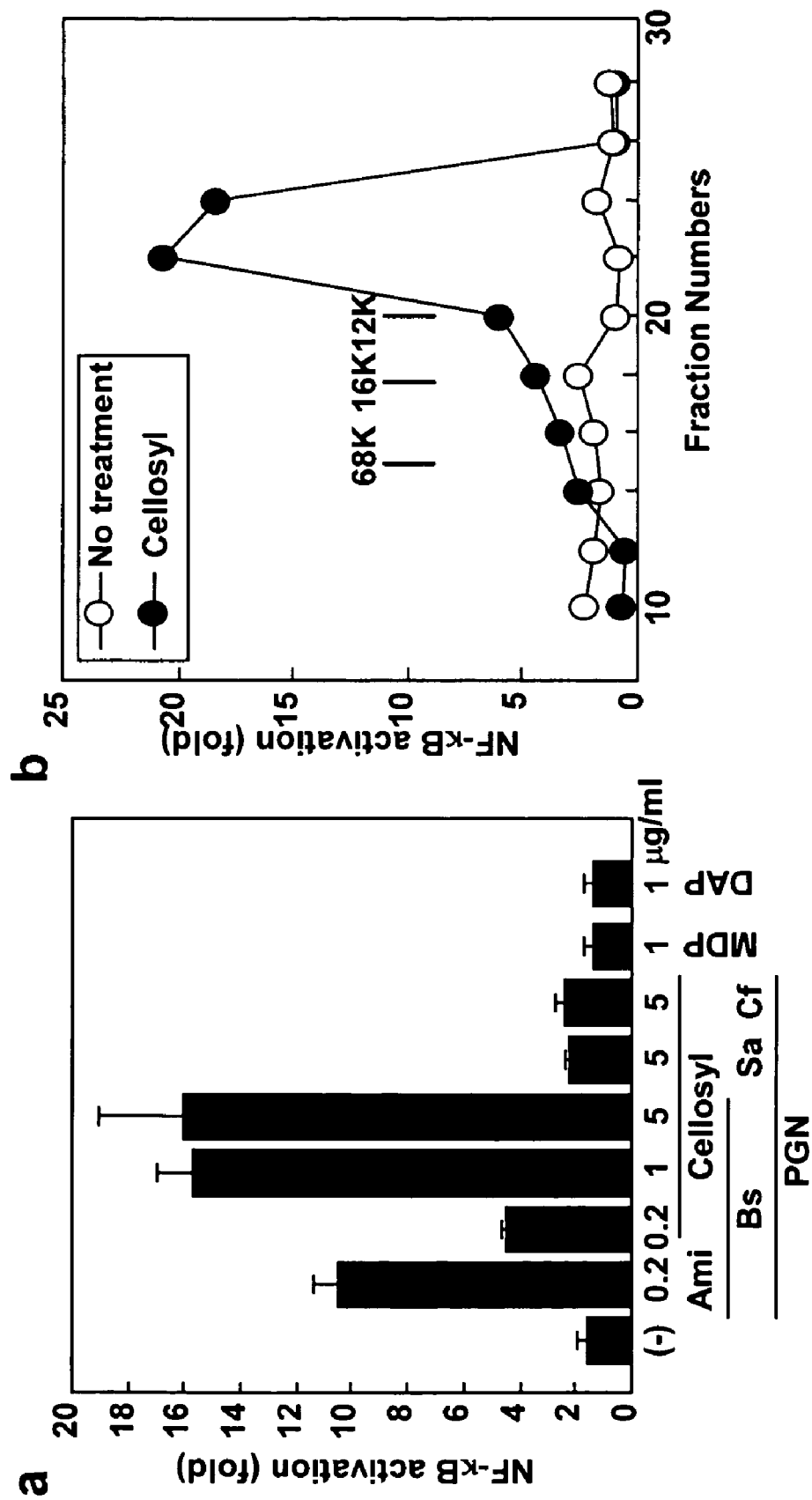
FIG. 3 shows that peptidoglycan from a subpopulation of bacteria stimulates NOD1. A) Cells were stimulated with the indicated amount of purified PGN from B. subtilis (Bs), S. aureus (Sa) and C. flaccumfaciens (Cf) PGN treated with recombinant AtlE amidase domain of S. epidermidis (Ami) or Cellosyl, or 1 μg of MDP or DAP. B) Cells were stimulated with SUPEROSE 12 gel-filtration fractions of soluble B. subtilis PGN with or without Cellosyl treatment. The NF-κB-dependent transcriptional activity of vector-transfected cells in the absence of the ligand is given as 1.

The results present in FIG. 2 suggested that PGN may be responsible for the NOD1-stimulatory activity. Cellosyl (i.e. a muramidase) and autolysin AltE (i.e. amidase domain) cleave the glycan chains and peptide interfaces of PGN, respectively, resulting in the release of muropeptides or glycan chains and desmuramylpeptide (DMP) (Heilman et al., Mol. Microbiol. 24:1013 [1997]; Atrih et al., J. Bact. 181:3956 [1999]). PGN from two Gram-positive bacteria, S. aureus and Curtobacterium flaccumfaciens do not contain DAP (Schleifer et al., Bacteriological Reviews 36:407 [1972]) and did not stimulate NOD1 (FIG. 3a). In contrast, PGN from B. subtilis, a Gram-positive bacterium that like E. coli has a DAP-containing PGN (Schleifer et al., supra), was able to activate NOD1 (FIG. 3a). Digestion of B. subtilis PGN with Cellosyl did not affect its ability to stimulate NOD1 (FIG. 3a), indicating that intact glycan strands are not required for activity. Moreover, digestion of PGN with amidase, which hydrolyses the bond between MurNAc and L-Ala, (FIG. 3) did not eliminate the ability of PGN to stimulate NOD1 (FIG. 3a). To further characterize the NOD1-stimulatory activity, PGN from B. subtilus was digested with Cellosyl and fractionated by gel-filtration chromatography. Analysis of each fraction revealed a major peak of NOD1-stimulating activity that was induced by Cellosyl digestion with a relative molecular mass of less than 12 kDa (FIG. 3b). The relative molecular mass of less than 12 kDa suggested that muropeptides that are generated upon Cellosyl digestion contain the NOD1-stimulatory activity.

Example 4

NOD1 Confers Responsiveness to γ-D-Glu-DAP and γ-D-Gln-DAP but not to MDP

Figure 4:
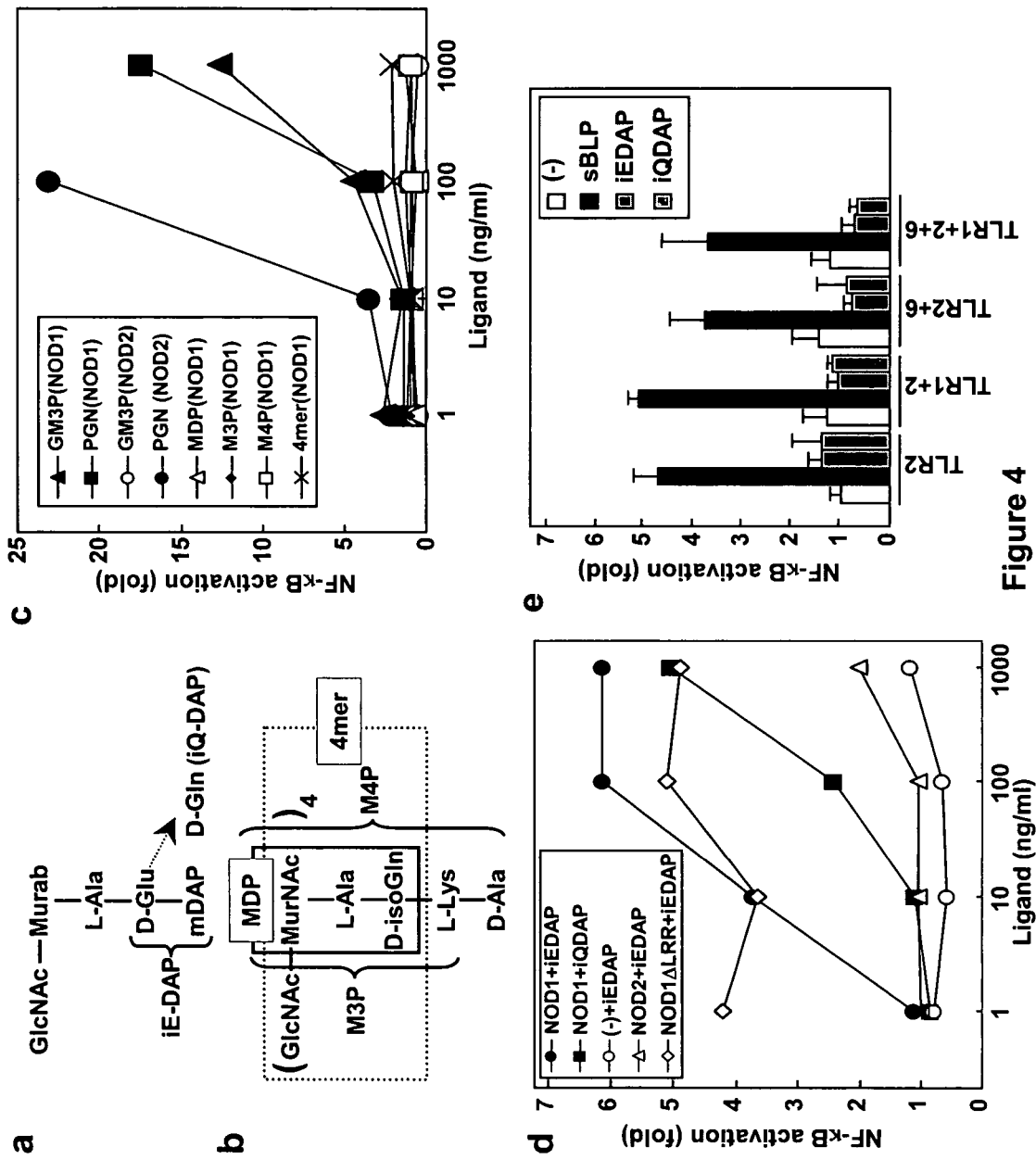
FIG. 4 shows stimulation of NOD1 by purified muropeptides and synthetic DMP. A) Structure of purified PGN fraction from B. subtilis (GM3P) and synthetic PGN-related compounds used in the study. B) Structure of MDP and four copies of GlcNAc-MurNAc with attached L-Ala-γ-D-Gln (4 mer) are indicated by closed and dotted boxes, respectively. C) The ability of cells were transfected with 0.3 ng pcDNA3-NOD1-Flag, 0.1 ng pcDNA3-Nod2 (NOD2) or vector control and reporter pBxIV-luc and pEF-BOS-β-gal plasmids to activate NF-κB. D) The ability of synthetic peptides, iE-DAP and iQ-DAP to stimulate NF-κB activation in the presence of control vector (−) and plasmids encoding NOD1 wild-type, mutant NOD1 lacking LRRs (NOD1ΔLRR) and NOD2. E) The ability of iE-DAP, iQ-DAP and sBLP (1 μg/ml) to activate NF-κB.

To determine if muropeptides containing DAP can stimulate NOD1, a highly purified fragment of B. subtilis PGN prepared by high performance liquid chromatography (HPLC), whose composition has been established by mass spectrometry (Atrih et al., supra), was tested. This muropeptide was composed of N-acetylglucosamine(GlcNAc)-N-acetyl-Muramicitol-L-Ala-γ-D-Glu-meso-DAP (GM3p) with a single amidation on DAP (Atrih et al., supra) (FIG. 4a), stimulated NOD1 in a dose-dependent manner (FIG. 4c). NOD2, a NOD protein family member highly related to NOD1, has been shown to mediate the recognition of MDP, a conserved molecule in PGN from most Gram-positive and Gram-negative bacteria (FIG. 4b). Neither MDP nor tetrameric forms of disaccharide dipeptide (4 mer) stimulated NOD1 (FIG. 4c). Furthermore, synthetic MurNAc-L-Ala-γ-D-Gln-L-Lys (M3P) and MurNAc-L-Ala-γ-D-Gln-L-Lys-D-Ala (M4P) also failed to stimulate NOD1 (FIG. 4b and FIG. 4c). These results suggested that NOD1 recognizes a DAP-containing molecule present in PGN that is distinct from MDP and MurNAc linked to L-Ala-γ-D-Gln-L-Lys-D-Ala (i.e. Lys-type PGN).

Previous studies demonstrated that both MDP and DMP derived from PGN stimulate human immune cells to induce secretion of cytokines and resistance against certain pathogens (Adam, supra). Because GlcNAc-N-acetyl-muramicitol-L-Ala-γ-D-Glu-meso-DAP (or GM3P), but neither MurNAc-L-Ala-γ-D-Gln-L-Lys-D-Ala (or M4P) nor MDP, did not display NOD1-stimulatory activity, it was contemplated that DAP or γ-D-Glu is important for NOD1 stimulation. A role for DAP or D-Glu in NOD1 stimulation was also suggested by the results presented in FIG. 2b, showing that reduction of PGN in LPS fraction which presumably destroys carboxyl residues resulted in the loss of NOD1-stimulatory activity. In addition, carbohydrate composition analysis of the partially purified Nod1-stimulatory component showed neither glucosamine nor muramic acid, suggesting that the carbohydrate chain is dispensable for NOD1-pathway induction. Together, these results suggested that DAP and/or γ-D-Glu containing peptides may be recognized by NOD1. To test this directly, the ability of synthetic iE-DAP and γ-D-Gln-DAP (iQ-DAP) to stimulate NOD1 was determined. Both synthetic peptides stimulated NOD1, but not TLR2 or TLR2 co-expressed with TLR1 and/or TLR6 (FIG. 4d and FIG. 4e). In contrast, synthetic lipoprotein activated TLR2 but not NOD1 (FIG. 4e). Notably, a mutant lacking the LRRs showed increased basal NF-κB activity compared with wild-type NOD1 as previously reported (Inohara et al., J. Biol. Chem. 274:14560 [1999]), but it did not respond to iE-DAP (FIG. 4d). This indicates that the LRRs are essential for recognition of both iE-DAP or iQ-DAP. Because DAP alone is unable to stimulate NOD1 (FIG. 3a), the results indicate that the dipeptide iE-DAP or iQ-DAP is the minimum structure of PGN required for NOD1 stimulation.

Example 5

NOD1 is Required for Cytokine Secretion in Response to iE-DAP

Figure 5:
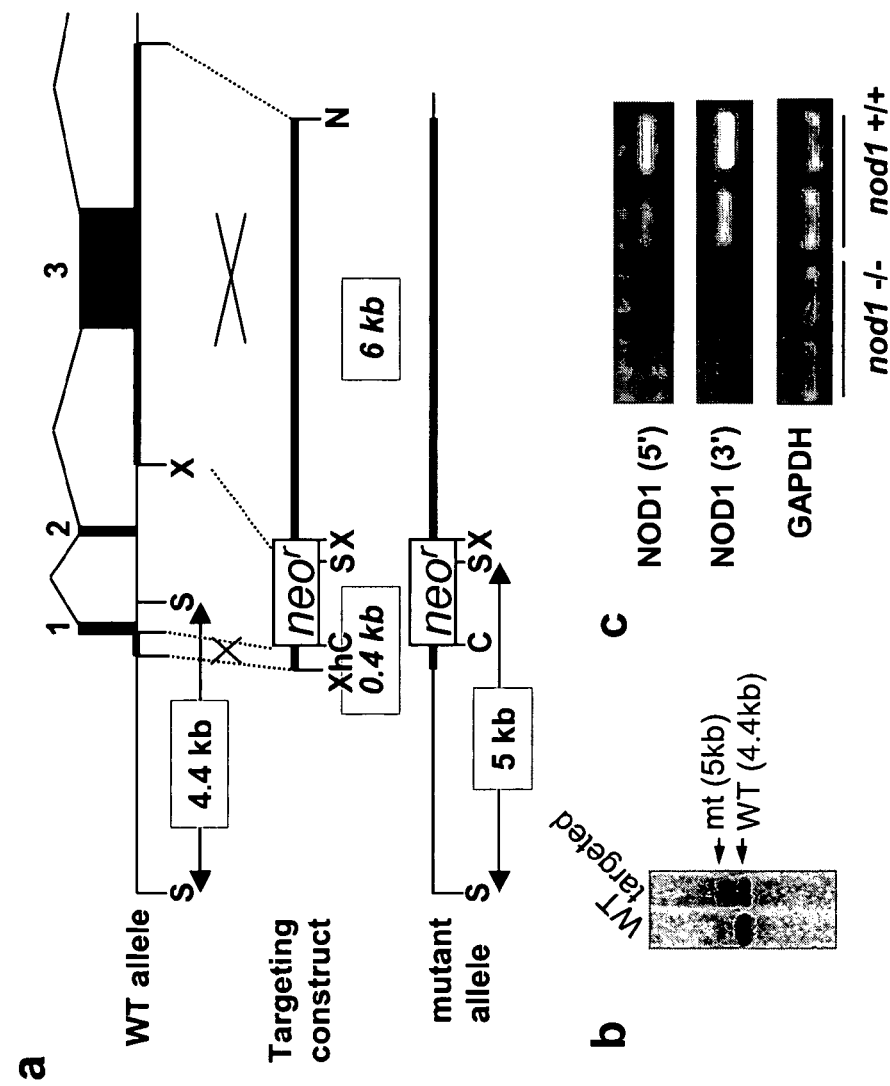
FIG. 5 shows the generation of Nod1 deficient mice. A) Schematic representation of the targeted Nod1 exons and wild-type (WT) allele, gene-targeting construct, and the targeted Nod1 allele (mt). B) Southern blot analysis of StuI-digested genomic DNA from wild-type and targeted ES clone using a DNA probe from 5' arm of the targeting vector. C) RT-PCR analysis of Nod1 expression in wild-type littermates (wt) and nod1-deficient mice using primers corresponding to the 5' and 3' coding regions of Nod1.
Figure 6:
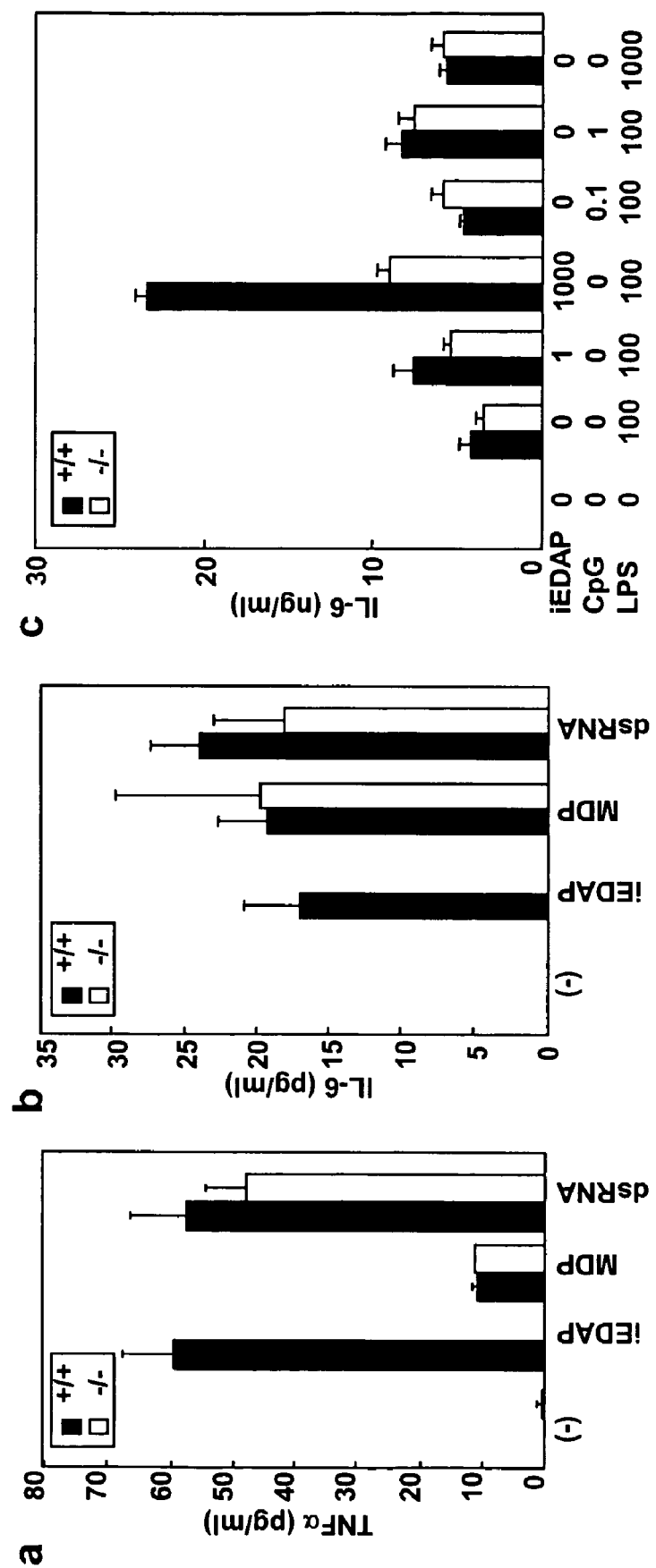
FIG. 6 shows the lack of cytokine production of nod1$^{-/-}$ macrophages in response to iE-DAP. A), B), C) $3\times10^5$ bone marrow-derived macrophages from wild-type littermates (wt) and nod1-deficient mice were stimulated with 100 ng/ml of iE-DAP, MDP or dsRNA for 12 hr A), B). 0, 100 ng/ml *Salmonella typhimurium* LPS was used in the presence of 0, 1, 1000 ng/ml iE-DAP or 0, 0.1 1 μM immunostimulatory CpG as indicated for 12 hr C) The concentration of TNF-α (a) and IL-6 (b,c) were determined by ELISA using specific antibodies. Values represent the mean of normalized data±S.D. of triplicate cultures.

PGN-derived iE-DAP is known to be the core structure in DMP capable of inducing the secretion of pro-inflammatory cytokines, including TNF-α, from immune cells (Adam, supra). To test if NOD1 is required for recognition of iE-DAP by macrophages, the ability of iE-DAP to stimulate cytokine secretion from macrophages derived from the bone marrow of wild-type and mutant mice lacking NOD1 was tested. Mice deficient in NOD1 were generated by gene targeting through homologous recombination. A gene targeting vector was constructed to replace the coding exons I and II of Nod1 with a neomycin-resistant cassette (FIG. 5a). The exons I and II encode the CARD of NOD1 which is essential for RICK binding and NF-κB activation (Inohara et al., J. Biol. Chem. 274:14560 [1999]). Homologous recombination in a positive ES clone was confirmed by Southern blot analysis (FIG. 5b). Inter-crosses of Nod1 +/− mice produced Nod1-deficient mice at the expected Mendelian ratio. Nod1-deficient mice were fertile, showed no gross abnormalities and appeared normal in a specific pathogen-free environment. The absence of Nod1 expression in cells from Nod1 −/− mice was confirmed by reverse-transcriptase (RT)-PCR analysis (FIG. 5c). Stimulation of mouse macrophages from wild-type mice with iE-DAP, MDP or double stranded RNA (dsRNA) induced the secretion of TNF-α and IL-6. By contrast, macrophages from littermate mutant mice lacking NOD1 responded to MDP and dsRNA but not to iE-DAP (FIGS. 6a and 6b). PGN and LPS are known to synergistically induce the secretion of cytokines in macrophages. To test whether iE-DAP can enhance the cellular response to LPS, macrophages from Nod1 +/+ and Nod1 −/− were stimulated with LPS and IE-DAP or CpG as a control. iE-DAP enhanced the secretion of IL-6 induced by LPS in wild-type macrophages and this effect was impaired in nod1 −/− mice (FIG. 6c). These results indicate that NOD1 is required for the response of macrophages to iE-DAP.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A method of screening compounds, comprising
   a) providing
      i) a cell expressing Nod1; and
      one or more test compounds, wherein said test compounds comprise a dipeptide, or an analog or small molecule mimetic thereof, wherein said dipeptide, or analog or small molecule mimetic thereof further comprises a glutamine-diaminopimelic acid dipeptide or a glutamic acid-diaminopimelic dipeptide;
   b) contacting said cell with said one or more test compounds; and
   c) determining the level of Nod1 activity in said cell in response to said one or more test compounds wherein said Nod1 activity is activation of NF-κB.

2. The method of claim 1, wherein said activation of NF-κB is detected using a reporter gene assay.

3. The method of claim 1, wherein said test compound is iE-DAP.

4. The method of claim 1, wherein said test compound is iQ-DAP.

5. The method of claim 1, wherein said Nod1 activity is increased in response to said test compound.

6. The method of claim 1, wherein said Nod1 activity is decreased in response to said test compound.

* * * * *